(12) United States Patent
Desenne et al.

(10) Patent No.: US 9,827,178 B2
(45) Date of Patent: Nov. 28, 2017

(54) COMPOSITION CONTAINING A VOLATILE LINEAR ALKANE, AN AMINATED SILICONE AND A VEGETABLE OIL

(75) Inventors: Patricia Desenne, Pringy (FR); Laurent Chesneau, Levallois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 12/970,988

(22) Filed: Dec. 17, 2010

(65) Prior Publication Data

US 2011/0150786 A1 Jun. 23, 2011

Related U.S. Application Data

(60) Provisional application No. 61/296,497, filed on Jan. 20, 2010.

(30) Foreign Application Priority Data

Dec. 23, 2009 (FR) ..................................... 09 59526

(51) Int. Cl.
| | | |
|---|---|---|
| *A61Q 5/12* | (2006.01) | |
| *A61Q 5/00* | (2006.01) | |
| *A61K 8/898* | (2006.01) | |
| *A61K 8/31* | (2006.01) | |
| *A61K 8/92* | (2006.01) | |

(52) U.S. Cl.
CPC ................ *A61K 8/31* (2013.01); *A61K 8/898* (2013.01); *A61K 8/922* (2013.01); *A61Q 5/00* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 3,818,105 A | | 6/1974 | Coopersmith et al. |
| 5,077,040 A | * | 12/1991 | Bergmann et al. ...... 424/70.122 |
| 6,132,743 A | * | 10/2000 | Kuroda et al. ................ 424/401 |
| 6,723,309 B1 | | 4/2004 | Deane |
| 2001/0028887 A1 | | 10/2001 | Douin et al. |
| 2006/0002879 A1 | * | 1/2006 | Chen et al. ................. 424/70.12 |
| 2006/0034791 A1 | * | 2/2006 | Shimizu et al. ........... 424/70.12 |
| 2009/0074695 A1 | | 3/2009 | Mahe et al. |
| 2009/0155198 A1 | | 6/2009 | Vic et al. |
| 2010/0183536 A1 | * | 7/2010 | Ansmann et al. .............. 424/65 |

FOREIGN PATENT DOCUMENTS

| | | |
|---|---|---|
| EP | 1 169 998 | 1/2002 |
| EP | 1888179 A1 * | 2/2008 |
| EP | 2 074 986 | 7/2009 |
| FR | 2 804 014 | 7/2001 |
| FR | 2 831 800 | 5/2003 |
| FR | 2 920 969 | 3/2009 |
| FR | 2 926 990 | 8/2009 |
| WO | WO 2007/052845 | 5/2007 |
| WO | WO 2008155057 A2 * | 12/2008 |

OTHER PUBLICATIONS

U.S. Appl. No. 12/977,183, filed Dec. 23, 2010, Desenne, et al.
U.S. Appl. No. 12/969,980, filed Dec. 16, 2010, Desenne, et al.
U.S. Appl. No. 12/975,705, filed Dec. 22, 2010, Desenne, et al.
U.S. Appl. No. 12/977,257, filed Dec. 23, 2010, Desenne, et al.
U.S. Appl. No. 12/977,204, filed Dec. 23, 2010, Desenne, et al.
U.S. Appl. No. 12/977,227, filed Dec. 23, 2010, Desenne, et al.
U.S. Appl. No. 12/975,632, filed Dec. 22, 2010, Desenne, et al.
French Search Report dated Oct. 20, 2010, in FR 09 59526, filed Dec. 23, 2009.
U.S. Appl. No. 14/683,345, filed Apr. 10, 2015, Desenne, et al.

* cited by examiner

*Primary Examiner* — John Pak
*Assistant Examiner* — Daniel Branson
(74) *Attorney, Agent, or Firm* — Oblon, McClelland, Maier & Neustadt, L.L.P.

(57) ABSTRACT

Composition containing, in a cosmetically acceptable medium, one or more volatile linear alkanes, at least 0.5 wt. % of one or more aminated silicones relative to the total weight of the cosmetic composition, and one or more vegetable oils different from the volatile linear alkanes. Use thereof for the treatment of keratinous materials, preferably of keratin fibres such as the hair.

11 Claims, No Drawings

COMPOSITION CONTAINING A VOLATILE LINEAR ALKANE, AN AMINATED SILICONE AND A VEGETABLE OIL

REFERENCE TO PRIOR APPLICATIONS

This application claims priority to U.S. provisional application Ser. No. 61/296,497, filed Jan. 20, 2010; and to French patent application 09 59526, filed Dec. 23, 2009, both incorporated herein by reference.

FIELD OF THE INVENTION

The present invention relates to a composition comprising one or more volatile linear alkane(s), one or more aminated silicone(s), and one or more vegetable oil(s), use thereof for the cosmetic treatment of keratinous materials, preferably of keratin fibres such as the hair and a method of cosmetic treatment of keratinous materials employing said composition.

BACKGROUND OF THE INVENTION

In the field of hair treatment, the use of volatile solvents is known in rinsed or non-rinsed hair care products. They are generally used for various reasons. They notably make it possible to modify the sensory effect of a hair product by imparting to it a light, non-tacky texture in the hand. They can also endow it with a slippery character that facilitates distribution of the product on the hair and in particular on dry hair.

In aqueous emulsions of the oil-in-water type, which can be in the form of more or less gelled creams, addition of volatile solvents can also permit solubilization of silicone gums which, based on their intrinsic viscosity, would be difficult to incorporate in the compositions.

These volatile solvents, which are generally of liquid fatty esters, hydrocarbon oils of the isododecane or isohexadecane type, and/or silicone oils, can notably induce problems of a greasy feel, lack of shine, and stiff, hard hair.

There is therefore a need to replace these volatile solvents, to avoid the aforementioned drawbacks.

BRIEF DESCRIPTION OF THE PREFERRED EMBODIMENTS

The inventors have discovered, unexpectedly and surprisingly, that by combining one or more volatile linear alkanes, one or more aminated silicones at a particular content, and one or more vegetable oils different from the volatile linear alkanes, it was possible to avoid the drawbacks mentioned above and improve the cosmetic properties such as smoothness, suppleness, disentangling, volume in particular by separation of the roots, and the tonicity of the hair.

In particular, the composition according to the invention makes it possible to obtain hair that is smoother, homogeneous and/or more supple, at the time of rinsing. On wet hair, hair is obtained that is easier to disentangle or is more tonic and/or has roots that are more separated (at the roots, the hair is not plastered down on the scalp but forms an angle, which gives volume). Hair treated with the composition according to the invention dries quickly. Moreover, the dry hair is more supple and/or smoother to the touch.

Thus, the invention relates to a cosmetic composition comprising, preferably in a cosmetically acceptable medium:

one or more volatile linear alkanes,
at least 0.5 wt. % of one or more aminated silicones, relative to the total weight of the cosmetic composition,
one or more vegetable oils different from the volatile linear alkanes.

It also relates to the use of a composition according to the invention for the cosmetic treatment of keratinous materials, preferably of keratin fibres such as the hair, notably as a rinsed hair care product.

Another object of the invention is a method of cosmetic treatment of keratinous materials, preferably of keratin fibres such as the hair, employing said composition.

"One or more volatile linear alkane(s)" means indiscriminately "one or more volatile linear alkane oil(s)".

A volatile linear alkane suitable for the invention is liquid at room temperature (about 25° C.) and at atmospheric pressure (101 325 Pa or 760 mmHg).

"Volatile linear alkane" suitable for the invention means a linear alkane that can evaporate in contact with the skin in less than one hour, at room temperature (25° C.) and at atmospheric pressure (101 325 Pa), which is liquid at room temperature, notably having a rate of evaporation in the range from 0.01 to 15 mg/cm$^2$/min, at room temperature (25° C.) and at atmospheric pressure (101 325 Pa).

Preferably, the volatile linear alkane or alkanes suitable for the invention have a rate of evaporation in the range from 0.01 to 3.5 mg/cm$^2$/min, preferably from 0.01 to 1.5 mg/cm$^2$/min, at room temperature (25° C.) and at atmospheric pressure (101 325 Pa).

More preferably, the volatile linear alkane or alkanes suitable for the invention have a rate of evaporation in the range from 0.01 to 0.8 mg/cm$^2$/min, preferably from 0.01 to 0.3 mg/cm$^2$/min, and even more preferably from 0.01 to 0.12 mg/cm$^2$/min, at room temperature (25° C.) and at atmospheric pressure (101 325 Pa).

The rate of evaporation of a volatile alkane according to the invention (and more generally of a volatile solvent) can notably be evaluated by the protocol described in WO 06/013413, and more particularly by the protocol described below.

Put 15 g of volatile hydrocarbon solvent in a crystallizing dish (diameter: 7 cm) placed on a balance that is in an enclosure of about 0.3 m3 with controlled temperature (25° C.) and humidity (relative humidity 50%).

Let the volatile hydrocarbon solvent evaporate freely, without stirring it, providing ventilation with a fan (PAPST-MOTOREN, reference 8550 N, operating at 2700 rev/min) arranged in a vertical position above the crystallizing dish containing the volatile hydrocarbon solvent, with the blades directed towards the crystallizing dish, at a distance of 20 cm relative to the bottom of the crystallizing dish.

Measure the mass of the volatile hydrocarbon solvent remaining in the crystallizing dish at regular intervals of time.

The evaporation profile of the solvent is then obtained by plotting the curve of the amount of product evaporated (in mg/cm$^2$) as a function of time (in min).

Then the rate of evaporation, which corresponds to the tangent at the origin of the curve obtained, is calculated. The rates of evaporation are expressed in mg of volatile solvent evaporated per unit area (cm$^2$) in unit time (minute).

According to a preferred embodiment, the volatile linear alkane or alkanes suitable for the invention have a non-zero vapour pressure (also called saturated vapour pressure), at room temperature, in particular a vapour pressure in the range from 0.3 Pa to 6000 Pa.

Preferably, the volatile linear alkane or alkanes suitable for the invention have a vapour pressure in the range from 0.3 to 2000 Pa, more preferably from 0.3 to 1000 Pa, at room temperature (25° C.).

More preferably, the volatile linear alkane or alkanes suitable for the invention have a vapour pressure in the range from 0.4 to 600 Pa, preferably from 1 to 200 Pa, and even more preferably from 3 to 60 Pa, at room temperature (25° C.).

According to one embodiment, a volatile linear alkane suitable for the invention can have a flash point in the range from 30 to 120° C., and more particularly from 40 to 100° C. The flash point is in particular measured according to standard ISO 3679.

According to one embodiment, the volatile linear alkane or alkanes suitable for the invention can be linear alkanes having from 7 to 15 carbon atoms, preferably from 8 to 14 carbon atoms, and more preferably from 9 to 14 carbon atoms.

More preferably, the volatile linear alkane or alkanes suitable for the invention have from 10 to 14 carbon atoms, and even more preferably from 11 to 14 carbon atoms.

The volatile linear alkane or alkanes suitable for the invention can advantageously be of vegetable origin.

Preferably, the volatile linear alkane or mixture of volatile linear alkanes present in the composition according to the invention comprises at least one 14C isotope of carbon (carbon 14). In particular, the 14C isotope can be present in a 14C/12C isotope ratio (by number of isotopes) greater than or equal to $1 \times 10^{-16}$, preferably greater than or equal to $1 \times 10^{-15}$, more preferably greater than or equal to $7.5 \times 10^{-14}$, and better still greater than or equal to $1.5 \times 10^{-13}$. Preferably, the 14C/12C isotope ratio is in the range from $6 \times 10^{-13}$ to $1.2 \times 10^{-12}$.

The quantity of 14C isotopes in the volatile linear alkane or mixture of volatile linear alkanes can be determined by methods known by a person skilled in the art such as Libby's counting method, liquid scintillation spectrometry or accelerator mass spectrometry.

Said alkane or mixture of alkanes can be obtained, directly or in several stages, from a vegetable raw material such as an oil, a butter, a wax, etc.

As examples of alkanes suitable for the invention, we may mention the alkanes described in patent applications WO 2007/068371 and WO2008/155059. These alkanes are obtained from fatty alcohols, themselves obtained from copra oil or palm oil.

As examples of linear alkanes suitable for the invention, we may mention n-heptane (C7), n-octane (C8), n-nonane (C9), n-decane (C10), n-undecane (C11), n-dodecane (C12), n-tridecane (C13), n-tetradecane (C14), and mixtures thereof. According to a particular embodiment, the volatile linear alkane is selected from n-nonane, n-undecane, n-dodecane, n-tridecane, n-tetradecane, and mixtures thereof, and better still from n-undecane, n-tridecane, and mixtures thereof.

According to a preferred embodiment, we may mention mixtures of n-undecane (C11) and of n-tridecane (C13), in particular obtained notably in examples 1 and 2 of application WO2008/155059.

We may also mention n-dodecane (C12) and n-tetradecane (C14) sold respectively under the references PARAFOL 12-97 and PARAFOL 14-97 by the company Sasol, and mixtures thereof.

One embodiment consists of using a single volatile linear alkane.

Alternatively, a mixture of at least two different volatile linear alkanes can be used, differing from one another in the number of carbons n by at least 1, in particular differing from one another in the number of carbons by 1 or by 2.

According to one embodiment, a mixture of at least two different volatile linear alkanes is used, having from 10 to 14 carbon atoms and differing from one another in the number of carbons by at least 1. As examples, we may notably mention the mixtures of volatile linear alkanes C10/C11, C11/C12, or C12/C13.

According to another embodiment, a mixture of at least two different volatile linear alkanes is used, having from 10 to 14 carbon atoms and differing from one another in the number of carbons by at least 2. As examples, we may notably mention the mixtures of volatile linear alkanes C10/C12, or C12/C14, for an even number of carbons n and the mixture C11/C13 for an odd number of carbons n.

According to a preferred embodiment, a mixture of at least two different volatile linear alkanes is used, having from 10 to 14 carbon atoms and differing from one another in the number of carbons by at least 2, and in particular a mixture of volatile linear alkanes C11/C13 or a mixture of volatile linear alkanes C12/C14. Advantageously, use of a mixture of n-undecane and n-tridecane is preferred.

Other mixtures combining more than 2 volatile linear alkanes according to the invention, such as, for example, a mixture of at least 3 different volatile linear alkanes having from 7 to 15 carbon atoms and differing from one another in the number of carbons by at least 1, can be used in the invention.

In the case of mixtures of two volatile linear alkanes, said two volatile linear alkanes preferably represent more than 95%, and more preferably more than 99 wt. % of the mixture.

According to a particular embodiment of the invention, in a mixture of volatile linear alkanes, the volatile linear alkane having the smallest number of carbons predominates in the mixture.

According to another embodiment of the invention, a mixture of volatile linear alkanes is used in which the volatile linear alkane having the largest number of carbons predominates in the mixture.

As examples of mixtures suitable for the invention, we may notably mention the following mixtures:

from 50 to 90 wt. %, preferably from 55 to 80 wt. %, more preferably from 60 to 75 wt. % of volatile Cn linear alkane with n in the range from 7 to 15, from 10 to 50 wt. %, preferably from 20 to 45 wt. %, preferably from 24 to 40 wt. %, of volatile Cn+x linear alkane with x greater than or equal to 1, preferably x=1 or x=2, with n+x between 8 and 14, relative to the total weight of the alkanes in said mixture.

In particular, said mixture of volatile linear alkanes can further contain:

less than 2 wt. %, preferably less than 1 wt. % of branched hydrocarbons, and/or less than 2 wt. %, preferably less than 1 wt. % of aromatic hydrocarbons, and/or less than 2 wt. %, preferably less than 1 wt. % and more preferably less than 0.1 wt. % of unsaturated hydrocarbons, said percentages being expressed relative to the total weight of the mixture.

More particularly, the volatile linear alkanes suitable for the invention can be used in the form of an n-undecane/n-tridecane mixture.

In particular, a mixture of volatile linear alkanes will be used comprising:

from 55 to 80 wt. %, preferably from 60 to 75 wt. % of C11 (n-undecane) volatile linear alkane and from 20 to 45 wt. %, preferably from 24 to 40 wt. % of C13 (n-tridecane) volatile linear alkane, relative to the total weight of the alkanes in said mixture.

According to a particular embodiment, the mixture of alkanes is an n-undecane/n-tridecane mixture. In particular, such a mixture can be obtained according to example 1 or example 2 of application WO 2008/155059. Use of said mixture imparts particularly advantageous cosmetic properties to the keratin fibres treated, notably in terms of suppleness and volume.

According to another particular embodiment, the n-dodecane sold under the reference PARAFOL 12-97 by SASOL is used.

According to another particular embodiment, the n-tetradecane sold under the reference PARAFOL 14-97 by SASOL is used.

According to yet another embodiment, a mixture of n-dodecane and of n-tetradecane is used, preferably in 85/15 ratio, such as the mixture marketed under the name VEGELIGHT 1214 by the company Biosynthis.

The composition of the invention preferably comprises from 0.5% to 90 wt. % of volatile linear alkane(s), in particular from 1% to 50 wt. %, more particularly from 3% to 40%, and better still from 3% to 30 wt. % of volatile linear alkane(s), relative to the total weight of the composition.

As already stated, the composition according to the present invention contains at least 0.5 wt. % of one or more aminated silicones, relative to the total weight of the composition.

"Aminated silicone" means any polyaminosiloxane, i.e. any polysiloxane having at least one primary, secondary, tertiary amine function or a quaternary ammonium group.

Preferably, the aminated silicone or aminated silicones used in the cosmetic composition according to the present invention are selected from:

(a) the compounds corresponding to the following formula (I):

(R1)$a$(T)3-$a$-Si[OSi(T)2]$n$-[OSi(T)$b$(R1)2-$b$]$m$-OSi(T)3-$a$-(R1)$a$     (I)

in which:

T is a hydrogen atom, or a phenyl, hydroxyl (—OH), or C1-C8 alkyl radical, and preferably methyl or C1-C8 alkoxy, preferably methoxy, a denotes the number 0 or an integer from 1 to 3, and preferably 0, b denotes 0 or 1, and in particular 1, m and n are numbers such that the sum (n+m) can vary notably from 1 to 2000 and in particular from 50 to 150, with n denoting a number from 0 to 1999 and notably from 49 to 149 and m denoting a number from 1 to 2000, and notably from 1 to 10;

R1 is a monovalent radical of formula -CqH2qL in which q is a number from 2 to 8 and L is an amino group optionally quaternized selected from the groups:

—N(R2)-CH2-CH2-N(R2)2;

—N(R2)2; —N+(R2)3Q-;

—N+(R2)(H)2Q-;

—N+(R2)2HQ-;

—N(R2)-CH2-CH2-N+(R2)(H)$_2$Q-, in which R2 denotes a hydrogen atom, a phenyl, a benzyl, or a saturated monovalent hydrocarbon radical, for example a C1-C20 alkyl radical, and Q-represents a halide ion such as for example fluoride, chloride, bromide or iodide.

In particular, the aminated silicones corresponding to the definition of formula (I) are selected from the compounds corresponding to the following formula (II):

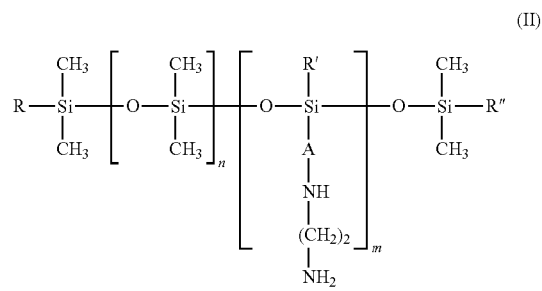

(II)

in which R, R', R", which may be identical or different, denote a C1-C4 alkyl radical, preferably CH3; a C1-C4 alkoxy radical, preferably methoxy; or OH; A represents a linear or branched, C3-C8, preferably C3-C6, alkylene radical; m and n are integers that depend on the molecular weight and whose sum is between 1 and 2000.

According to a first possibility, R, R', R", which may be identical or different, represent a C1-C4 alkyl radical or hydroxyl radical, A represents a C3 alkylene radical, and m and n are such that the weight-average molecular weight of the compound is between about 5000 and 500 000. Compounds of this type are called "amodimethicone" in the CTFA dictionary.

According to a second possibility, R, R', R", which may be identical or different, represent a C1-C4 alkoxy radical or hydroxyl radical, at least one of the radicals R or R" is an alkoxy radical and A represents a C3 alkylene radical. The hydroxy/alkoxy molar ratio is preferably between 0.2/1 and 0.4/1 and advantageously equal to 0.3/1. Moreover, m and n are such that the weight-average molecular weight of the compound is between 2000 and 106. More particularly, n is between 0 and 999 and m is between 1 and 1000, the sum of n and m being between 1 and 1000.

In this category of compounds, we may mention, among others, the product Belsil® ADM 652, marketed by Wacker.

According to a third possibility, R, R", which are different, represent a C1-C4 alkoxy radical or hydroxyl radical, at least one of the radicals R, R" is an alkoxy radical, R' represents a methyl radical and A represents a C3 alkylene radical. The hydroxy/alkoxy molar ratio is preferably between 1/0.8 and 1/1.1, and advantageously is equal to 1/0.95.

Moreover, m and n are such that the weight-average molecular weight of the compound is between 2000 and 200000. More particularly, n is between 0 and 999 and m is between 1 and 1000, the sum of n and m being between 1 and 1000.

More particularly, we may mention the product FluidWR® 1300, marketed by Wacker.

According to a fourth possibility, R, R" represent a hydroxyl radical, R' represents a methyl radical and A is a C4-C8, preferably C4, alkylene radical. Moreover, m and n are such that the weight-average molecular weight of the compound is between 2000 and 106. More particularly, n is between 0 and 1999 and m is between 1 and 2000, the sum of n and m being between 1 and 2000.

A product of this type is notably marketed under the name DC28299 by Dow Corning.

Note that the molecular weight of these silicones is determined by gel permeation chromatography (room temperature, polystyrene standard; columns µ styragem; eluent THF; flow of 1 mm/m; inject 200 µl of a 0.5 wt. % solution of silicone in THF and use detection by refractometry and with a UV-meter).

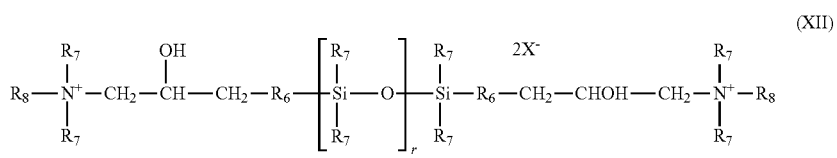

A product corresponding to the definition of formula (I) is in particular the polymer called "trimethylsilylamodimethicone" in the CTFA dictionary (7th edition 1997), corresponding to the following formula (III):

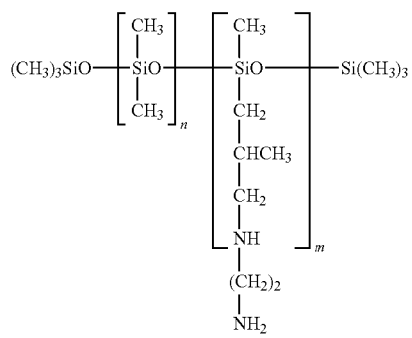

in which n and m have the meanings given above according to formula (I) or (II).

Such compounds are described for example in EP 0095238; a compound of formula (III) is for example sold under the name Q2-8220 by the company OSI.

(b) the compounds corresponding to the following formula (IV):

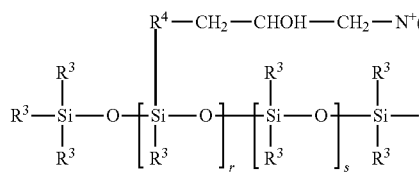

in which:
R3 represents a monovalent C1-C18 hydrocarbon radical, and in particular a C1-C18 alkyl radical or C2-C18 alkenyl radical, for example methyl;
R4 represents a divalent hydrocarbon radical, notably a C1-C18 alkylene radical or a divalent C1-C18, for example C1-C8, alkyleneoxy radical;

Q- is a halide ion, notably chloride;
r represents an average random value from 2 to 20 and in particular from 2 to 8;
s represents an average random value from 20 to 200 and in particular from 20 to 50.

Such compounds are described more particularly in U.S. Pat. No. 4,185,087.

A compound included in this class is that sold by the company Union Carbide under the name "Ucar Silicone ALE 56".

(c) the quaternary ammonium silicones of formula (V):

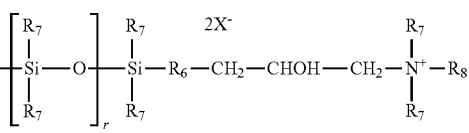

in which:
R7, which may be identical or different, represent a monovalent hydrocarbon radical having from 1 to 18 carbon atoms, and in particular a C1-C18 alkyl radical, a C2-C18 alkenyl radical or a ring comprising 5 or 6 carbon atoms, for example methyl;
R6 represents a divalent hydrocarbon radical, notably a C1-C18 alkylene radical or a divalent C1-C18, for example C1-C8, alkyleneoxy radical joined to the Si by an SiC bond;
R8, which may be identical or different, represent a hydrogen atom, a monovalent hydrocarbon radical having from 1 to 18 carbon atoms, and in particular a C1-C18 alkyl radical, a C2-C18 alkenyl radical, a radical —R6-NHCOR7;
X— is an anion such as a halide ion, notably chloride or a salt of an organic acid (acetate etc.);
r represents an average random value from 2 to 200 and in particular from 5 to 100.

These silicones are for example described in application EP-A-0530974.

As a compound of formula (V), we may mention the product referred to in the CTFA dictionary (1997 Edition) under the name Quaternium 80 such as that offered by the company EVONIK GOLDSCHMIDT under the names ABIL QUAT 3272 or 3474.

d) the aminated silicones of the following formula:

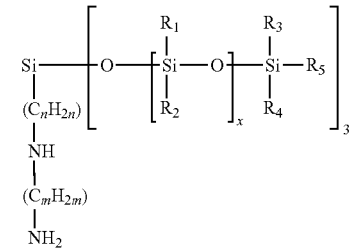

in which:
R1, R2, R3 and R4, which may be identical or different, denote a C1-C4 alkyl radical or a phenyl group,
R5 denotes a C1-C4 alkyl radical or a hydroxyl group,
n is an integer in the range from 1 to 5,
m is an integer in the range from 1 to 5,
and in which x is selected in such a way that the amine index is between 0.01 and 1 meq/g.

The aminated silicone or aminated silicones that are particularly preferred are the polysiloxanes with amino groups such as the compounds of formula (II) or of formula (III), and even more particularly the silicones with quaternary ammonium groups of formula (V).

Preferably the weight ratio of the amount of volatile linear alkane(s) to the amount of aminated silicone(s) varies from 0.5 to 100, more preferably from 0.5 to 50, and better still from 1 to 20.

When these compounds are used, a particularly interesting embodiment is their joint use with cationic and/or non-ionic surfactants.

For example it is possible to use the product sold under the name "Emulsion Cationique DC939" by the company Dow Corning, which comprises, apart from amodimethicone, a cationic surfactant, namely trimethylcetylammonium chloride, and a non-ionic surfactant of formula: C13H27-(OC2H4)12-OH, known by the CTFA designation "trideceth-12".

Another commercial product usable according to the invention is the product sold under the name "Dow Corning Q2 7224" by the company Dow Corning, comprising, together with the trimethylsilylamodimethicone of formula (C) described above, a non-ionic surfactant of formula: C8H17-C6H4-(OCH2CH2)40-OH, known by the CTFA designation "octoxynol-40", a second non-ionic surfactant of formula: C12H25-(OCH2-CH2)6-OH, known by the CTFA designation "isolaureth-6", and propylene glycol.

The aminated silicone or aminated silicones are present in the composition according to the invention in an amount of at least 0.5 wt. %, preferably in an amount in the range from 0.5 to 20 wt. %, more particularly in an amount in the range from 0.5 to 10 wt. %, and better still in an amount in the range from 0.75 to 5 wt. %, relative to the total weight of the composition.

The composition according to the invention contains one or more vegetable oils.

"Oil" means any lipophilic, non-ionic compound, insoluble in water and liquid at room temperature (25° C.) and at atmospheric pressure (760 mmHg, or 101 325 Pa). "Insoluble in water" means, in the sense of the present invention, a compound whose solubility at spontaneous pH in water at 25° C. and at atmospheric pressure is less than 1%, and preferably less than 0.5 wt. %. The oils are soluble in organic solvents in the same conditions of temperature and pressure, for example chloroform, ethanol or benzene. Moreover, the oils are liquid at normal temperature (25° C.) and at atmospheric pressure. The oils preferably have a melting point below 5° C. and a viscosity less than 500 cP at 25° C. at a shear rate of 1 s-l.

In particular, "vegetable oil" means an oil as defined above, extracted from a species belonging to the vegetable kingdom.

The vegetable oil or vegetable oils used according to the invention are different from the volatile linear alkanes as defined previously and are selected from the vegetable oils usually employed in the cosmetics field.

As examples of vegetable oil usable in compositions of the invention, we may mention:
sweet almond oil,
argan oil,
avocado oil,
peanut oil,
camellia oil,
safflower oil,
calophyllum oil,
colza oil,
copra oil,
coriander oil,
cucurbit oil,
wheatgerm oil,
jojoba oil or jojoba liquid wax,
linseed oil,
macadamia oil,
maize germ oil,
hazelnut oil,
walnut oil,
vernonia oil,
apricot kernel oil,
olive oil,
evening primrose oil,
palm oil,
passionflower oil,
grapeseed oil,
rose oil,
castor oil,
rye oil,
sesame oil,
rice bran oil,
soya oil, and
sunflower oil.

The vegetable oils according to the invention generally have not undergone chemical transformation after extraction.

Among the vegetable oils mentioned above, it is preferable to use olive oil, argan oil, avocado oil, colza oil, jojoba oil or jojoba liquid wax, soya oil, sunflower oil, and more preferably avocado oil, jojoba oil or jojoba liquid wax.

Preferably, the vegetable oil or vegetable oils are present in the composition in an amount in the range from 0.3 to 30%, more preferably in an amount in the range from 1 to 20%, and better still in an amount in the range from 3 to 15 wt. %, relative to the total weight of the composition.

The composition according to the invention can further comprise one or more surfactants selected from anionic, amphoteric or zwitterionic, non-ionic and cationic surfactants.

Among the anionic surfactants usable according to the invention, we may notably mention the salts, in particular alkali metal salts and notably sodium salts, the ammonium salts, the salts of amines, the salts of aminoalcohols or the magnesium salts of the following compounds: alkylsulphates, alkylethersulphates, alkyl amidoethersulphates, monoglyceride sulphates, alkylglycerylsulphonates, alkyl sulphonates, alkylphosphates, alkylamidesulphonates, alkarylsulphonates, α-olefin sulphonates, paraffin sulphonates, alkylsulphosuccinates, alkylethersulphosuccinates, alkylamidesulphosuccinates, alkylsulphosuccinamates, alkylsulphoacetates, alkyletherphosphates, acylisethionates, N-acyltaurates, N-acylamino acids such as N-acylsarcosinates and N-acylglutamates. We may also mention as anionic surfactants that can be used in compositions according to the invention, salts of fatty acids such as salts of undecenylic, oleic, ricinoleic, palmitic and stearic acids, acids of copra oil or of hydrogenated copra oil and acylhydroxyacids such as acyl-lactylates. It is also possible to use weakly anionic surfactants such as alkyl D-galactoside uronic acids and salts thereof as well as polyoxyalkylated alkyl ether alkylamidoethercarboxylic acids or salts thereof, the alkyl or acyl radical of these various compounds preferably having from 8 to 22 carbon atoms and the anionic derivatives of alkyl (C8-C22) polyglycosides (sulphate, sulphosuccinate, phosphate, isethionate, ethercarboxylate, carbonate).

Among the amphoteric surfactants usable according to the invention, we may notably mention the derivatives of secondary or tertiary aliphatic amines, in which the aliphatic radical is a linear or branched chain having 8 to 22 carbon atoms and containing at least one hydrosolubilizing anionic group, for example a carboxylate, sulphonate, sulphate, phosphate or phosphonate group. We may also mention, among the amphoteric or zwitterionic surfactants, the sulphobetaines, alkyl amidoalkylbetaines, alkylamidoalkyl-sulphobetaines, imidazolium derivatives such as those of amphocarboxyglycinate or of amphocarboxypropionate.

Among the non-ionic surfactants usable according to the invention, we may notably mention the polyethoxylated polypropoxylated or polyglycerolated derivatives of alcohols or of alphadiols or of alkylphenols or of fatty acids, having a fatty chain with from 8 to 28 carbon atoms, and the number of ethylene oxide or propylene oxide groups can range from 2 to 50 and that of glycerol notably from 2 to 30. We may also mention the copolymers of ethylene oxide and propylene oxide, the condensates of ethylene oxide and propylene oxide on fatty alcohols, polyethoxylated fatty amides preferably having from 2 to 30 moles of ethylene oxide, polyglycerolated fatty amides having on average 1 to 5 glycerol groups, polyglycerolated diglycolamides, esters of sorbitan fatty acids optionally ethoxylated, esters of sucrose fatty acids, esters of polyoxyalkylated fatty acids, alkylpolyglycosides optionally oxyalkylated, esters of alkylglucosides, derivatives of N-alkylglucamine and of N-acylmethylglucamine, aldobionamides and amine oxides.

"Cationic surfactant" means a surfactant that is positively charged when it is contained in the composition according to the invention. This surfactant can bear one or more permanent positive charges or contain one or more cationizable functions within the composition according to the invention.

Among the cationic surfactants usable in the composition according to the invention, we may notably mention primary, secondary or tertiary fatty amines, optionally polyoxyalkylated, or salts thereof, the quaternary ammonium salts, and mixtures thereof.

As quaternary ammonium salts, we may notably mention, for example:
those having the following general formula (VII):

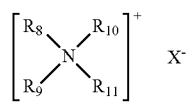

(VII)

in which the radicals R8 to R11, which may be identical or different, represent a linear or branched aliphatic radical, having from 1 to 30 carbon atoms, or an aromatic radical such as aryl or alkaryl, at least one of the radicals R8 to R11 denoting a radical having from 8 to 30 carbon atoms, preferably from 12 to 24 carbon atoms. The aliphatic radicals can comprise heteroatoms such as notably oxygen, nitrogen, sulphur and the halogens.

The aliphatic radicals are for example selected from alkyl, alkoxy, polyoxyalkylene (C2-C6), alkylamide, alkyl(C12-C22)amidoalkyl(C2-C6), alkyl(C12-C22)acetate, hydroxyalkyl radicals, having from about 1 to 30 carbon atoms; X— is an anion selected from the group comprising halides, phosphates, acetates, lactates, alkyl(C2-C6)sulphates, alkyl- or alkaryl-sulphonates;
the quaternary ammonium salts of imidazoline, for example those of the following formula (VIII):

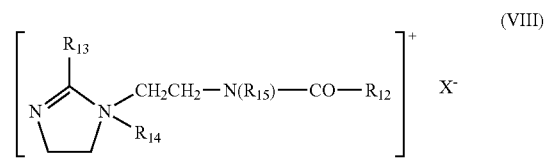

(VIII)

in which R12 represents an alkenyl or alkyl radical having from 8 to 30 carbon atoms, for example derivatives of tallow fatty acids, R13 represents a hydrogen atom, a C1-C4 alkyl radical or an alkenyl or alkyl radical having from 8 to 30 carbon atoms, R14 represents a C1-C4 alkyl radical, R15 represents a hydrogen atom, a C1-C4 alkyl radical, X— is an anion selected from the group comprising halides, phosphates, acetates, lactates, alkylsulphates, alkyl- or alkaryl-sulphonates. Preferably, R12 and R13 denote a mixture of alkenyl or alkyl radicals having from 12 to 21 carbon atoms, for example derivatives of tallow fatty acids, R14 denotes a methyl radical, R15 denotes a hydrogen atom. Such a product is marketed for example under the name REWOQUAT® W 75 by the company REWO;
the quaternary diammonium salts of formula (IX):

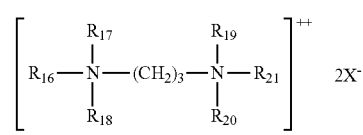

(IX)

in which R16 denotes an aliphatic radical having from about 16 to 30 carbon atoms, R17, R18, R19, R20 and R21, which may be identical or different, are selected from hydrogen or an alkyl radical having from 1 to 4 carbon atoms, and X— is an anion selected from the group comprising halides, acetates, phosphates, nitrates and methylsulphates. Said quaternary diammonium salts notably comprise propane tallow diammonium dichloride;
the quaternary ammonium salts containing at least one ester function, such as those of the following formula (X):

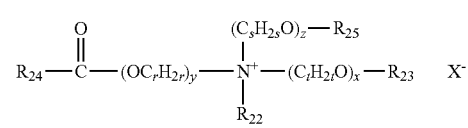

(X)

in which:
R22 is selected from the C1-C6 alkyl radicals and C1-C6 hydroxyalkyl or dihydroxyalkyl radicals;
R23 is selected from:
the radical

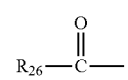

the radicals R27 which are linear or branched, saturated or unsaturated C1-C22 hydrocarbon radicals,
the hydrogen atom, R25 is selected from:
the radical

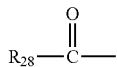

the radicals R29 which are linear or branched, saturated or unsaturated C1-C6 hydrocarbon radicals,
the hydrogen atom,
R24, R26 and R28, which may be identical or different, are selected from linear or branched, saturated or unsaturated C7-C21 hydrocarbon radicals;
r, s and t, which may be identical or different, are integers with a value from 2 to 6;
y is an integer with a value from 1 to 10;
x and z, which may be identical or different, are integers with a value from 0 to 10;
X— is a simple or complex, organic or inorganic anion;
provided that the sum x+y+z has a value from 1 to 15, that when x has the value 0 then R23 denotes R27 and that when z has the value 0 then R25 denotes R29.

The alkyl radicals R22 can be linear or branched and more particularly linear.

Preferably R22 denotes a methyl, ethyl, hydroxyethyl or dihydroxypropyl radical, and more particularly a methyl or ethyl radical.

Advantageously, the sum x+y+z has a value from 1 to 10.

When R23 is an R27 hydrocarbon radical, it can be long and can have from 12 to 22 carbon atoms, or short and have from 1 to 3 carbon atoms.

When R25 is an R29 hydrocarbon radical, it preferably has 1 to 3 carbon atoms.

Advantageously, R24, R26 and R28, which may be identical or different, are selected from linear or branched, saturated or unsaturated C11-C21 hydrocarbon radicals, and more particularly from linear or branched, saturated or unsaturated alkyl and C11-C21 alkenyl radicals.

Preferably, x and z, which may be identical or different, have the value 0 or 1.

Advantageously, y is equal to 1.

Preferably, r, s and t, which may be identical or different, have a value of 2 or 3, and even more particularly are equal to 2.

The anion X— is preferably a halide (chloride, bromide or iodide) or an alkyl sulphate, more particularly methyl-sulphate. However, it is possible to use methanesulphonate, phosphate, nitrate, tosylate, an anion derived from an organic acid such as acetate or lactate or any other anion compatible with ammonium with an ester function.

The anion X— is even more particularly chloride or methylsulphate.

More particularly, in the composition according to the invention, the ammonium salts of formula (X) are used in which:
R22 denotes a methyl or ethyl radical,
x and y are equal to 1;
z is equal to 0 or 1;
r, s and t are equal to 2;
R23 is selected from:
the radical

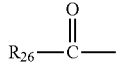

the methyl, ethyl or C14-C22 hydrocarbon radicals,
the hydrogen atom;
R25 is selected from:
the radical

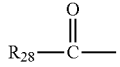

the hydrogen atom;
R24, R26 and R28, which may be identical or different, are selected from linear or branched, saturated or unsaturated C13-C17 hydrocarbon radicals, and preferably from linear or branched, saturated or unsaturated C13-C17 alkyl and alkenyl radicals.

Advantageously, the hydrocarbon radicals are linear.

We may mention for example the compounds of formula (X) such as the diacyloxyethyl-dimethylammonium, diacyloxyethyl-hydroxyethyl-methylammonium, monoacyloxyethyl-dihydroxyethyl-methylammonium, triacyloxy ethyl-methylammonium, monoacyloxyethyl-hydroxyethyl-dimethyl ammonium salts (notably chloride or methylsulphate), and mixtures thereof. The acyl radicals preferably have 14 to 18 carbon atoms and are derived more particularly from a vegetable oil such as palm oil or sunflower oil. When the compound contains several acyl radicals, the latter can be identical or different.

These products are obtained, for example, by direct esterification of triethanolamine, triisopropanolamine, alkyldiethanolamine or alkyldiisopropanolamine optionally oxyalkylated on fatty acids or on mixtures of fatty acids of vegetable or animal origin, or by transesterification of their methyl esters. This esterification is followed by quaternization using an alkylating agent such as an alkyl (preferably methyl or ethyl) halide, a dialkyl (preferably methyl or ethyl) sulphate, methyl methanesulphonate, methyl para-toluenesulphonate, glycol chlorohydrin or glycerol chlorohydrin.

Such compounds are marketed for example under the names DEHYQUART® by the company HENKEL, STEPANQUAT® by the company STEPAN, NOXAMIUM® by the company CECA, REWOQUAT® WE 18 by the company REWO-WITCO.

The composition according to the invention preferably contains a mixture of quaternary ammonium mono-, di- and triester salts with a majority by weight of diester salts.

As the mixture of ammonium salts, it is possible to use for example a mixture containing 15 to 30 wt. % of acyloxyethyl-dihydroxyethyl-methylammonium methylsulphate, 45 to 60% of diacyloxyethyl-hydroxyethyl-methylammonium methylsulphate and 15 to 30% of triacyloxyethyl-methylammonium methylsulphate, the acyl radicals having from 14 to 18 carbon atoms and derived from palm oil, optionally partially hydrogenated.

It is also possible to use the ammonium salts containing at least one ester function described in U.S. Pat. Nos. 4,874,554 and 4,137,180.

Among the quaternary ammonium salts of formula (VII), on the one hand the tetraalkylammonium chlorides are preferred, for example the dialkyldimethylammonium or alkyltrimethylammonium chlorides in which the alkyl radical has from about 12 to 22 carbon atoms, in particular the behenyltrimethylammonium, distearyldimethylammonium, cetyltrimethylammonium, benzyldimethylstearylammonium chlorides or, on the other hand, distearoylethyl hydroxyethyl methylammonium methosulphate, dipalmitoylethylhydroxyethylammonium methosulphate or dicetylaroylethylhydroxyethylammonium methosulphate, or, finally, palmitylamidopropyltrimethylammonium chloride or stearamidopropyldimethyl-(myristyl acetate)-ammonium chloride marketed under the name CERAPHYL® 70 by the company VAN DYK.

Among all the cationic surfactants that can be present in the composition according to the invention, it is preferable to select the cationic surfactant or surfactants from the cetyltrimethylammonium (INCI cetrimonium-), behenyltrimethylammonium (INCI behentrimonium-), dipalmitoylethylhydroxyethylammonium, distearoylethylhydroxyethyl methylammonium, methyl alkyl(C9-C19) alkyl(C10-C20) amidoethylimidazolium, stearamidopropyldimethylammonium salts (chloride or methosulphate), or mixtures thereof.

Advantageously, the surfactant or surfactants are selected from the non-ionic surfactants and the cationic surfactants When the composition comprises at least one surfactant, the latter is present at a concentration preferably in the range from 0.1 to 20 wt. %, and more preferably from 0.2 to 10 wt. %, of the total weight of the composition.

The composition used according to the invention comprises a cosmetically acceptable medium.

The cosmetically acceptable medium is constituted of water or of a mixture of water and at least one cosmetically acceptable solvent preferably selected from the C1-C4 lower alcohols, such as ethanol, isopropanol, tert-butanol or n-butanol; the polyols such as glycerol, propylene glycol and polyethylene glycols; and mixtures thereof.

The composition according to the invention can further comprise one or more conventional additives well known in the art, different from the compounds defined previously. As examples of additives usable according to the invention, we may mention associative or non-associative polymers, ionic or non-ionic and in particular cationic polymers, liquid or solid fats different from vegetable oils, non-aminated silicones, silanes, proteins, vitamins, reducing agents, plasticizers, emollients, anti-foaming agents, hydrating agents, pigments, clays, mineral fillers, UV filters, mineral colloids, peptizing agents, solubilizers, perfumes, preservatives, luster agents, propellants, and mineral or organic thickeners; these additives being different from the compounds defined above.

A person skilled in the art will take care to select any additive or additives and their amount in such a way that they do not adversely affect the properties of the compositions of the present invention.

The additive or additives are generally present in the composition according to the invention in an amount in the range from 0 to 20 wt. % relative to the total weight of the composition.

The compositions according to the invention can be in the form of rinsed or non-rinsed care compositions, the latter being in the form of a lotion of varying thickness, a cream, a gel or an emulsion.

Another object of the invention is the use of the cosmetic composition as described above for the cosmetic treatment of keratinous materials, preferably of keratin fibres such as the hair, and notably as a rinsed hair product.

The invention also relates to a method of cosmetic treatment of keratinous materials, preferably of keratin fibres such as the hair, which comprises the application of an effective amount of a cosmetic composition as described above, on said materials, and optionally rinsing of said composition after an optional pause.

When the composition according to the invention is applied in the form of a lotion or a cream, it is optionally left on the hair for about 0.5 to 5 minutes, and is then rinsed optionally with water.

The following examples are given for the purpose of illustrating the present invention.

In the following examples, all quantities are stated as percentage by weight of product as such relative to the total weight of the composition, unless stated otherwise.

EXAMPLE 1

Comparison

The following rinsed care compositions A, B were prepared from the ingredients shown in the following table.

|  | Compositions | |
|---|---|---|
|  | A comparative | B invention |
| Cyclopentadimethylsiloxane (Xiameter PMX-0245 cyclosiloxane - Dow Corning) | 3 | — |
| Mixture of n-undecane and n-tridecane according to example 2 of application WO 2008/155059 | — | 3 |
| Polydimethylsiloxane with aminoethylaminopropyl groups in non-ionic microemulsion at 17 wt. % in water (Wacker Belsil ADM Log 1 - Wacker) | 5 | 5 |
| Jojoba liquid wax | 6 | 6 |
| Avocado oil | 5 | 5 |
| Ethyl alcohol, 96° | 17 | 17 |
| Glycerol | 4 | 4 |
| Behenyl trimethyl ammonium chloride at 79 wt. % of active substance (Genamin KDMP - Clariant) | 2 | 2 |
| Polyethylene glycol monoisostearate with 8 moles of ethylene oxide | 2 | 2 |
| Perfume | qs | qs |
| Deionized water | Qs 100 | Qs 100 |

Composition A was compared with composition B according to the invention.

6 grams of composition A was applied on one half of the head and 6 grams of composition B on the other half of the head of a model. After massaging the hair, it was rinsed with water.

The suppleness of the hair during rinsing, the separation of the roots of the wet hair and the rate of drying of the hair were evaluated.

This evaluation was performed on a panel of 10 models by experts trained regularly in this exercise. For each criterion evaluated, scores were attributed in the range from 0 (not good) to 5 (very good).

The following results were observed:
Comparison of compositions A and B

|  | A comparative | B invention |
|---|---|---|
| Suppleness of the hair fibre during rinsing in water | 3.5 | 4.0 |
| Separation of the roots on wet hair | 1.4 | 2.0 |

Composition B according to the invention leads to better softening of the hair fibres during rinsing, and on wet hair, with more volume (there is better separation of the roots).

Quicker drying was also observed for the hair treated with composition B relative to the comparative composition A.

EXAMPLE 2

Another Rinsed Care Composition According to the Invention

| Composition | C invention |
|---|---|
| Mixture of n-dodecane and n-tetradecane (VEGELIGHT 1214 - Biosynthis) | 3 |
| Polydimethylsiloxane with aminoethylaminopropyl groups in non-ionic microemulsion at 17 wt. % in water (Wacker Belsil ADM Log 1 -Wacker) | 5 |
| Jojoba liquid wax | 6 |
| Avocado oil | 5 |
| Ethyl alcohol, 96° | 17 |
| Glycerol | 4 |
| Behenyl trimethyl ammonium chloride at 79 wt. % of active substance (Genamin KDMP - Clariant) | 2 |
| Polyethylene glycol monoisostearate with 8 moles of ethylene oxide | 2 |
| Perfume | qs |
| Deionized water | Qs 100 |

The hair treated with composition C has the same properties as that treated with composition B.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising, in a cosmetically acceptable medium:
from 3 to 30% of a mixture of 55 to 80% wt. % of a volatile $C_n$ linear alkane with n being from 7 to 15, and from 20 to 25 wt. % of a volatile $C_{n+x}$ linear alkane with x being greater than or equal to 1, relative to the total weight of alkanes in the mixture,
0.75 to 5 wt. % of one or more aminated silicones of formula (II) relative to the total weight of said composition,
from 3 to 15% of one or more vegetable oils different from the volatile linear alkanes:

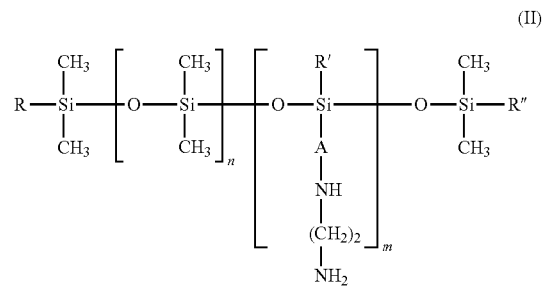

in which R, R', R", which may be identical or different, denote a $C_1$-$C_4$ alkyl radical; a C1-$C_4$ alkoxy radical; or OH; A represents a linear or branched $C_3$-$C_8$ alkylene radical; and m and n are integers whose sum is between 1 and 2000; and
wherein the composition does not comprise any other polymers except for optionally cationic polymers.

2. A composition according to claim 1, wherein the volatile linear alkane or alkanes are selected from n-heptane (C7), n-octane (C8), n-nonane (C9), n-decane (C10), n-undecane (C11), n-dodecane (C12), n-tridecane (C13), n-tetradecane (C14), and mixtures thereof.

3. A composition according to claim 1, wherein the volatile linear alkane or alkanes are selected from n-nonane, n-undecane, n-dodecane, n-tridecane, n-tetradecane, and mixtures thereof.

4. A composition according to claim 1, wherein the volatile linear alkanes are selected from mixtures of n-undecane and n-tridecane.

5. A composition according to claim 1, wherein the volatile linear alkane or alkanes are of vegetable origin.

6. A composition according to claim 1, wherein:
(i) R, R', R", which may be identical or different, represent a C1-C4 alkyl radical or a hydroxyl, A represents a C3 alkylene radical, and m and n are such that the weight-average molecular weight of the compound is between about 5000 and 500,000,
(ii) R, R', R", which may be identical or different, represent a C1-C4 alkoxy radical or hydroxyl radical, at least one of the radicals R or R" being an alkoxy radical, A represents a C3 alkylene radical, and m and n are such that the weight-average molecular weight of the compound is between 2000 and 106,
(iii) R, R", which are different, represent a C1-C4 alkoxy radical or hydroxyl radical, at least one of the radicals R, R" being an alkoxy radical, R' represents a methyl radical, A represents a C3 alkylene radical, and m and n are such that the weight-average molecular weight of the compound is between 2000 and 200,000, or
(iv) R, R" represent a hydroxyl radical, R' represents a methyl radical, A is a C4-C8 alkylene radical, and m and n are such that the weight-average molecular weight of the compound is between 2000 and 106.

7. A composition according to claim 1, wherein the vegetable oil or oils are selected from:

sweet almond oil,
argan oil,
avocado oil,
peanut oil,
camellia oil,
safflower oil,
calophyllum oil,
colza oil,
copra oil,
coriander oil,
cucurbit oil,
wheatgerm oil,
jojoba oil or jojoba liquid wax,
linseed oil,
macadamia oil,
maize germ oil,
hazelnut oil,
walnut oil,
vernonia oil,
apricot kernel oil,
olive oil,
evening primrose oil,
palm oil,
passionflower oil,
grapeseed oil,
rose oil,
castor oil,
rye oil,
sesame oil,
rice bran oil,
soya oil,
sunflower oil
and mixtures thereof.

8. A composition according to claim 1, further comprising at least one additive selected from the group consisting of associative or non-associative polymers, cationic polymers, liquid or solid fats different from the vegetable oils, non-aminated silicones, silanes, proteins, vitamins, reducing agents, plasticizers, emollients, anti-foaming agents, hydrating agents, pigments, clays, mineral fillers, UV filters, mineral colloids, peptizing agents, solubilizers, perfumes, preservatives, lustre agents, propellants, and mineral and organic thickeners.

9. The composition according to claim 1, wherein the volatile linear alkane to the aminated silicone are present in a ratio of 1 to 20.

10. A method, comprising application of the composition according to claim 1 to a keratin material.

11. The method according to claim 10, wherein the keratin material is hair.

* * * * *